United States Patent
Somani et al.

(10) Patent No.: US 6,534,494 B1
(45) Date of Patent: Mar. 18, 2003

(54) PROCESS FOR THE PREPARATION OF CEFUROXIME AXETIL IN AN AMORPHOUS FORM

(75) Inventors: Jitendra Krishan Somani, Gurgaon (IN); Sanjeev Sethi, Faridabad (IN); Om Dutt Tyagi, New Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/673,929

(22) PCT Filed: Jan. 27, 1999

(86) PCT No.: PCT/IB99/00145

§ 371 (c)(1), (2), (4) Date: Dec. 18, 2000

(87) PCT Pub. No.: WO99/65919

PCT Pub. Date: Dec. 23, 1999

Related U.S. Application Data

(63) Continuation of application No. 09/098,513, filed on Jun. 17, 1998, now Pat. No. 6,060,599.

(51) Int. Cl.[7] ..................... C07D 501/02; A61K 31/546
(52) U.S. Cl. ....................................... 514/202
(58) Field of Search ............................ 540/222; 514/202

(56) References Cited

U.S. PATENT DOCUMENTS

| 4,267,320 | A |   | 5/1981  | Gregson et al. |            |
| 4,562,181 | A |   | 12/1985 | Crisp et al.   |            |
| 4,820,833 | A |   | 4/1989  | Crisp et al.   |            |
| 4,865,851 | A | * | 9/1989  | James et al.   | 424/493    |
| 4,897,270 | A | * | 1/1990  | Deutsch et al. | 424/465    |
| 4,994,567 | A |   | 2/1991  | Crisp et al.   |            |
| 5,013,833 | A |   | 5/1991  | Crisp et al.   |            |
| 5,118,799 | A |   | 6/1992  | Rossignol      |            |
| 5,409,917 | A | * | 4/1995  | Miyake et al.  | 514/202    |
| 5,677,443 | A | * | 10/1997 | Zenoni         | 540/215    |
| 5,741,807 | A | * | 4/1998  | Thomas         | 514/399    |
| 5,847,118 | A |   | 12/1998 | Karimian et al.|            |
| 6,169,102 | B1| * | 1/2001  | Kanamaru et al.| 514/376    |
| 6,306,391 | B1| * | 10/2001 | Modi et al.    | 424/93.44  |

FOREIGN PATENT DOCUMENTS

| GB | 2145409    | * | 3/1985  |
| WO | WO 98/43980|   | 10/1998 |

* cited by examiner

Primary Examiner—Mark L Berch
(74) Attorney, Agent, or Firm—Jayadeep R. Deshmukh, Esq.

(57) ABSTRACT

A process for preparing cefuroxime axetil in substantially amorphous form comprises forming a mixture of crystalline cefuroxime axetil and at least one pharmaceutically acceptable excipient, and subjecting the mixture to milling for a period of time sufficient to convert the crystalline cefuroxime axetil to substantially amorphous form, i.e., the crystallinity is less than 5%. The amorphous cefuroxime axetil has a chemical purity of at least 95%. Desirably, the particles of the milled material are reduced to a size of less than 2.

6 Claims, 13 Drawing Sheets

PROCESS FOR THE PREPARATION OF CEFUROXIME AXETIL IN AN AMORPHOUS FORM

This application is a 371 of PCT/IB99/00145 filed Jan. 27, 1999 which is a continuation of Ser. No. 09/098,513 filed Jun. 17, 1998, now U.S. Pat. No. 6,060,599.

BACKGROUND OF THE INVENTION

Cefuroxime axetil is the 1-acetoxyethyl ester of cefuroxime, a cephalosporin antibiotic with a broad spectrum of activity against gram-positive and gram-negative microorganisms. This compound, as well as many other esters of cefuroxime, are disclosed and claimed in U.S. Pat. No. 4,267,320 (Gregson et al.; May 12, 1981). According to this patent, the presence of an appropriate esterifying group, such as the 1-acetoxyethyl group of cefuroxime axetil, enhances absorption of cefuroxime from the gastrointestinal tract, whereupon the esterifying group is hydrolyzed by enzymes present in the human body. Because of the presence of an asymmetric carbon atom, cefuroxime axetil can be produced as R and S diastereoisomers, or as a racemic mixture of the R and S diastereoisomers. U.S. Pat. No. 4,267,320 discloses conventional methods for preparing a mixture of the R and S isomers in crystalline form, as well as for separating the individual R and S diastereoisomers.

U.S. Pat. No. 4,562,181 (Crisp et al.; Dec. 31, 1985), and the related U.S. Pat. No. 4,820,833 (Apr. 11, 1989); U.S. Pat. No. 4,994,567 (Feb. 19, 1991); and U.S. Pat. No. 5,013,833 (May 7, 1991), disclose that cefuroxime axetil in amorphous form, essentially free from crystalline material and having a purity of at least 95% aside from residual solvents, has a higher bioavailability than the crystalline form while also having adequate chemical stability. These patents disclose that highly pure cefuroxime axetil can be recovered in substantially amorphous form from a solution containing cefuroxime axetil by spray drying roller drying, or solvent precipitation. The preferred method is spray drying. In each case crystalline cefuroxime axetil is dissolved in an organic solvent and the cefuroxime axetil is recovered from the solution in a highly pure, substantially amorphous form by one of the foregoing methods.

For purposes of patient safety, it is highly desirable to limit the amount of residual solvent present in any medicament administered to a patient. Therefore, it is an objective of the present invention to obtain a highly pure, substantially amorphous form of cefuroxime axetil in admixture with one or more pharmaceutically acceptable excipients without the use of organic solvents as have been heretofore used. Preparing highly pure cefuroxime axetil in substantially amorphous form provides benefits with respect to safety, health, and environmental considerations. Thus, the amorphous product should be at least as free of residual solvents as the starting crystalline material.

SUMMARY OF THE INVENTION

In accordance with the present invention, a method is disclosed for preparing highly pure cefuroxime axetil in substantially amorphous form in admixture with one or more pharmaceutically acceptable excipients. The method of the present invention comprises forming a mixture of crystalline cefuroxime axetil and the pharmaceutically acceptable excipient(s), and subjecting this mixture to milling action, whereby a composition is obtained in which the cefuroxime axetil has a purity by chromatographic analysis (chemical purity) of at least 95%, and the cefuroxime axetil is substantially free of any crystalline material, i.e., contains less than about 5% crystalline material. The amorphous cefuroxime axetil made in accordance with this invention may comprise either of the R or S diastereoisomers, or a mixture of the two. Desirably the particle size of the milled material is less than 2 μm.

The milling may be carried out manually using a mortar and pestle. Alternatively, the milling may be carried out using commercially available milling machines, such as the ones described herein below.

DETAILED DESCRIPTION OF THE INVENTION

According to the present invention, cefuroxime axetil is obtained in a highly pure, substantially amorphous form in admixture with one or more pharmaceutically acceptable excipients by milling crystalline cefuroxime axetil together with the pharmaceutically acceptable excipient. Crystalline cefuroxime axetil may be prepared by the methods described in the previously mentioned U.S. patents, which are incorporated herein by reference. The pharmaceutically acceptable excipient(s) can be one or more of any known inert solid materials used in the formulation of dosage forms. Pharmaceutical excipients well known in the pharmaceutical arts can be found listed, e.g., in *Handbook of Pharmaceutical Excipients Handbook* (Eds. A. Wade and P. J. Weller, Second Edition, 1994; The Pharmaceutical Press, London), the U.S. FDA listing of inactive ingredients, and other sources of pharmaceutical literature. Examples include sodium chloride, calcium carbonate, lactose, starch, microcrystalline cellulose, colloidal silica, talc, sodium lauryl sulphate, and the like.

According to the present invention, cefuroxime axetil in a highly pure, substantially amorphous form having a chromatographic (chemical) purity of at least 95% is obtained in admixture with one or more pharmaceutically acceptable excipients by milling a mixture of highly pure crystalline cefuroxime axetil (chromatographic purity at least 95%) and the excipient(s) until the mixture is substantially free of any crystalline material. Both the starting crystalline material and the final substantially amorphous form may consist of the individual R and S diastereoisomers, or a racemic mixture of the two.

In accordance with one aspect of the present invention, the crystalline cefuroxime axetil is milled by grinding action between two surfaces. Such milling has been traditionally carried out in pharmacy practice by compounding using a pestle and mortar. According to the invention milling machines that work on substantially the same principle may be used in the present process. Examples of such milling machines include various makes of ball mills, roller mills, gyratory mills, and the like.

Figure 1:
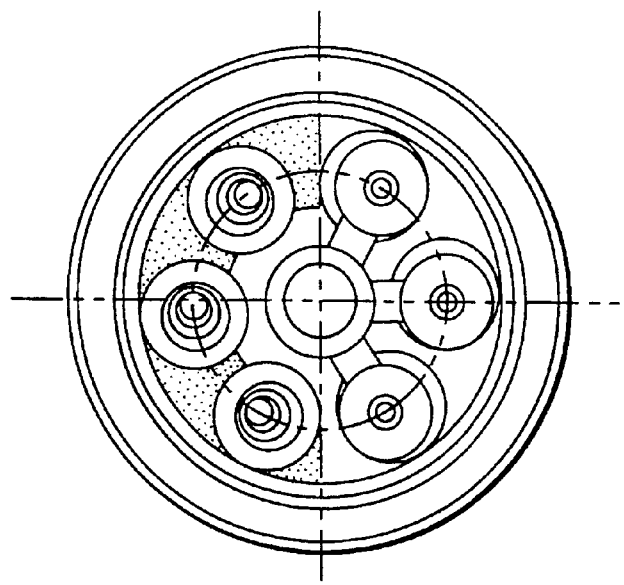
FIG. 1 is a schematic diagram of one commercially available milling machine suitable for carrying out the process of the present invention.

In a preferred embodiment of the invention, a mill such as a Micros Super Fine Mill (available from Nara Machinery Co., Ltd. of Tokyo, Japan) is used. This mill, schematically illustrated in FIG. 1, consists of a water cooled jacketed bowl (10) with the inside surface (12) made of a suitable material such as zirconium oxide, stainless steel, tungsten carbide, or aluminum oxide. The mill has a centrally located main shaft (14) to which are attached radially positioned subshafts (16) such that when the main shaft rotates, the subshafts revolve around the periphery of the vessel. Surrounding the subshafts are freely movable rings (18) made of suitable material such as zirconium oxide. Each ring can move freely. Thus, as the central shaft rotates, the rings acquire a planetary motion consisting of revolutions around the central shaft and rotations around the subshaft. The particles are thus subjected to a grinding action between the rings (18) and the wall surface (12). A compressive force is generated due to the centrifugal force on the rings simultaneously with friction created between the moving surfaces. Depending on the size of the mill, the speed of rotation of the main shaft and the effective volume of the grinding chamber may vary. The effective volume of the grinding chamber may be in the range from about 0.45 liters to about 30 liters. For low capacity mills (Micros '0', capacity 0.45 liters; Micros 5, capacity 4.8 liters), the speed of rotation of the main shaft is typically in the range from about 500 rpm to about 2000 rpm.

According to the invention, the Micros Super Fine Mill is typically charged with feed material such that from about 10% to 30% of the effective volume of the grinding chamber is occupied. Examples of methods of transferring materials well known in the art include manual transfer, gravity feed, pneumatic conveying (using a high velocity air stream), and vacuum transfer. Such methods, well known in the art, may be used with the process of this invention to charge the feed material into the grinding volume available between the bowl and the subshafts. For satisfactory operation of the Micros Super Fine Mill, the drug and the pharmaceutically acceptable excipient may be mixed in a wide range of ratios, for example, from about 1:20 to about 100:1; however, in preferred embodiments of the invention, the ratio of drug to excipient is from about 24:1 to about 2:1, more preferably from about 15:1 to about 5:1. It is believed that the pharmaceutically acceptable excipient aids in forming the amorphous cefuroxime axetil by acting as a diluent interposing itself between drug particles, and thereby preventing consolidation or bonding between drug particle surfaces.

The pharmaceutically acceptable excipients useful in the present invention include, but are not limited to, sodium lauryl sulphate, talc, colloidal silica, sodium chloride, calcium carbonate, starch, or mixtures thereof. In more preferred embodiments, the pharmaceutically acceptable excipient is selected from sodium lauryl sulphate, colloidal silica and mixtures thereof. In a most preferred embodiment of the invention, the cefuroxime axetil is milled in a Micros Super Fine Mill together with sodium lauryl sulphate (10% w/w) and colloidal silica (2% w/w).

The period of milling using the Micros Super Fine Mill will vary depending on the size of the mill, the speed of rotation of the main shaft, the type of feed material, and the quantity of feed material. The effects of these variables are well known in the art and the invention may be worked over a range of these variables. Typically, the period of milling ranges from about 15 mins. to 300 mins.

Generally, the drug and pharmaceutically acceptable excipient(s), in a ratio from about 15:1 to about 5:1, are milled together in a Micros '0' Super Fine Mill for about 120 mins. with the speed of rotation of the main shaft in the range from about 800 to 2000 rpm.

Alternatively, the drug and pharmaceutically acceptable excipient(s), in a ratio from about 15:1 to about 5:1, are milled together in a Micros '5' Super Fine Mill for a period from about 90 to 240 mins. The speed of rotation of the main shaft is in the range from about 400 to 700 rpm.

According to preferred embodiments of the invention, the crystalline cefuroxime axetil (R, S, or racemic mixture) is milled by grinding action between surfaces such that the particle size of the milled material is reduced to less than 2 μm.

Figure 2:
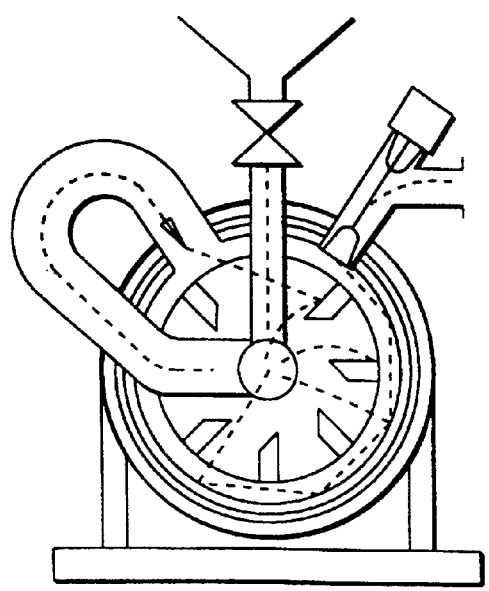
FIG. 2 is a schematic diagram of a second commercially available milling machine suitable for carrying out the process of the present invention.

According to another aspect of the invention, the cefuroxime axetil is subjected to milling involving attrition of the particles by collisions between particles, and between particles and machine surfaces. An example of a milling machine operating on this mode of operation is a Nara Hybridization System (Nara Machinery Co., Ltd., Tokyo, Japan). The Nara Hybridization System, schematically illustrated in FIG. 2, consists of a mixer (40), a feeder (42), a hybridizer (44), a collector (not shown), and a control panel (46). The hybridizer, the milling component of the system, consists of a rotator (48), a stator (50), blades (52) attached to the stator, an outer cooling jacket (54), a cycle tube (56), and a powder outlet valve (58). The feeder transfers a defined quantity of feed material into the hybridizer. The blades rotating at a high speed generate an air stream that carries the powder mixture and circulates it repeatedly through the cycle tube. The particles collide at a high velocity with each other, the blades, and the stator. Nara Hybridization Systems are available in various sizes from a capacity of 3.5 Kg/hr to 50 Kg/hr.

According to the invention, the Nara Hybridizing System is operated by milling a mixture of drug and pharmaceutically acceptable excipient in a ratio from about 1:7 to about 3:2, more preferably from about 1:4 to about 1:1. In more preferred embodiments of the invention, a mixture consisting of 3 parts by weight of cefuroxime axetil and 7 parts by weight of starch are subjected to milling in a Nara Hybridization System. The period of milling may vary depending on the size of the mill, the velocity of the blades, the type of feed material and the quantity of feed material. The period of milling may typically range from about 30 mins. to 240 mins.

The present invention is illustrated by the following examples which are not intended to limit the scope of the invention.

Examples 1 to 9 illustrate the process of obtaining cefuroxime axetil in a highly pure, substantially amorphous form by milling involving grinding a mixture of crystalline cefuroxime axetil and the pharmaceutically acceptable excipient(s) between two surfaces. Example 10 illustrates the process of obtaining cefuroxime axetil in an amorphous form by milling involving attrition of particles by collisions with other particles or machine surfaces.

EXAMPLE 1

Figure 3:
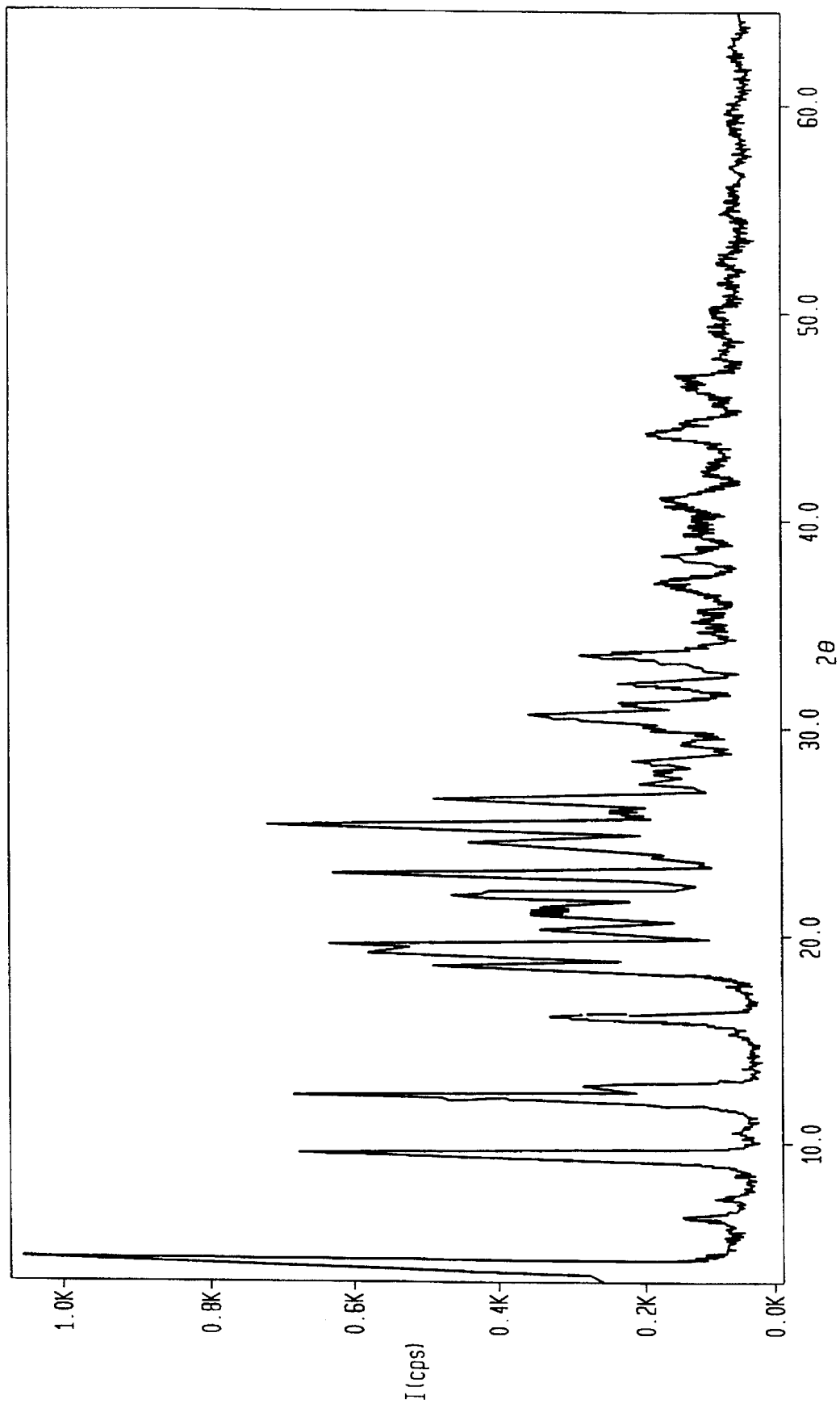
FIG. 3 is an x-ray powder diffraction (XRD) pattern showing peaks characteristic of crystalline S-cefuroxime axetil.
Figure 4:
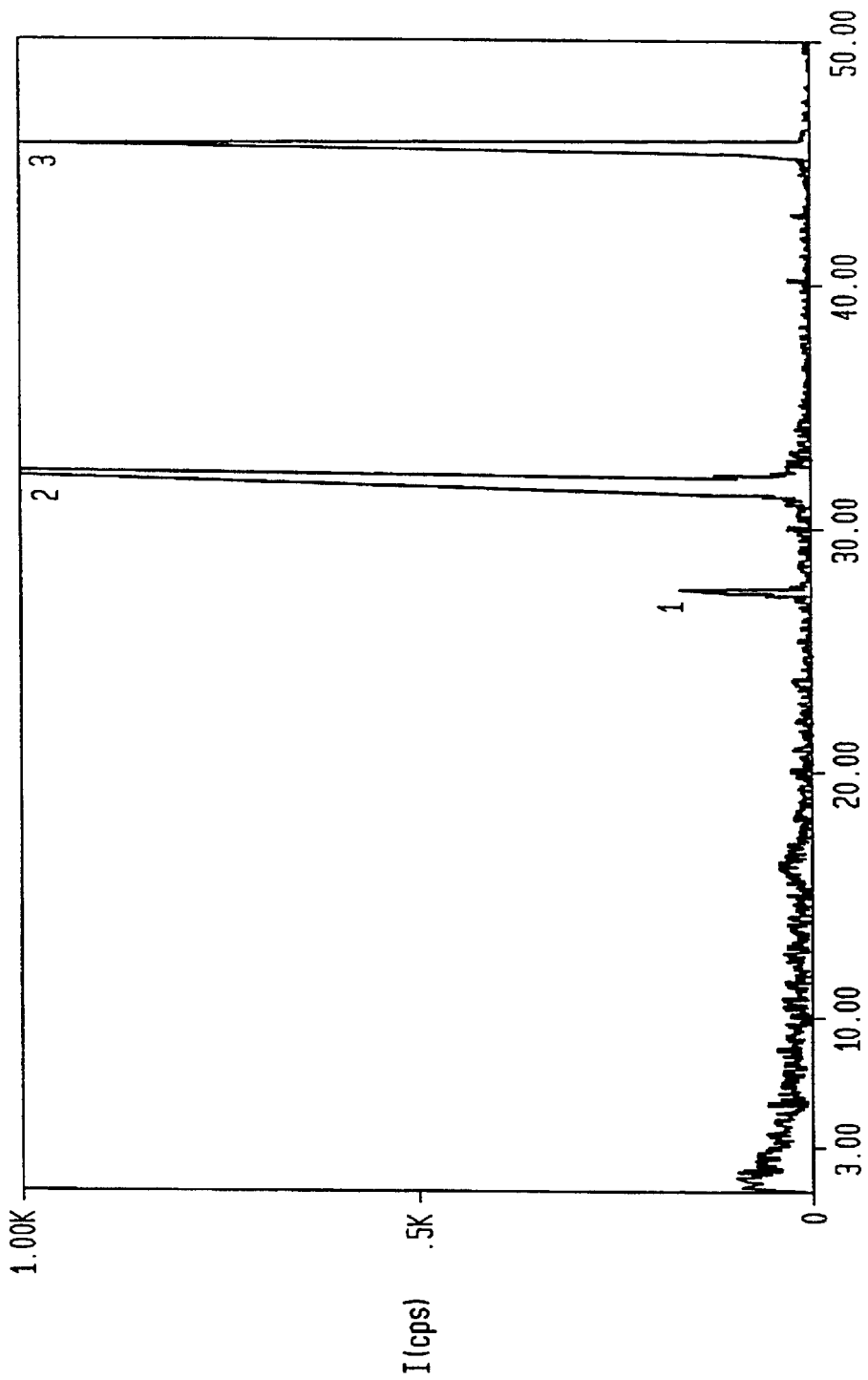
FIG. 4 is the XRD pattern of sodium chloride, a typical pharmaceutical excipient used with cefuroxime axetil.
Figure 5:
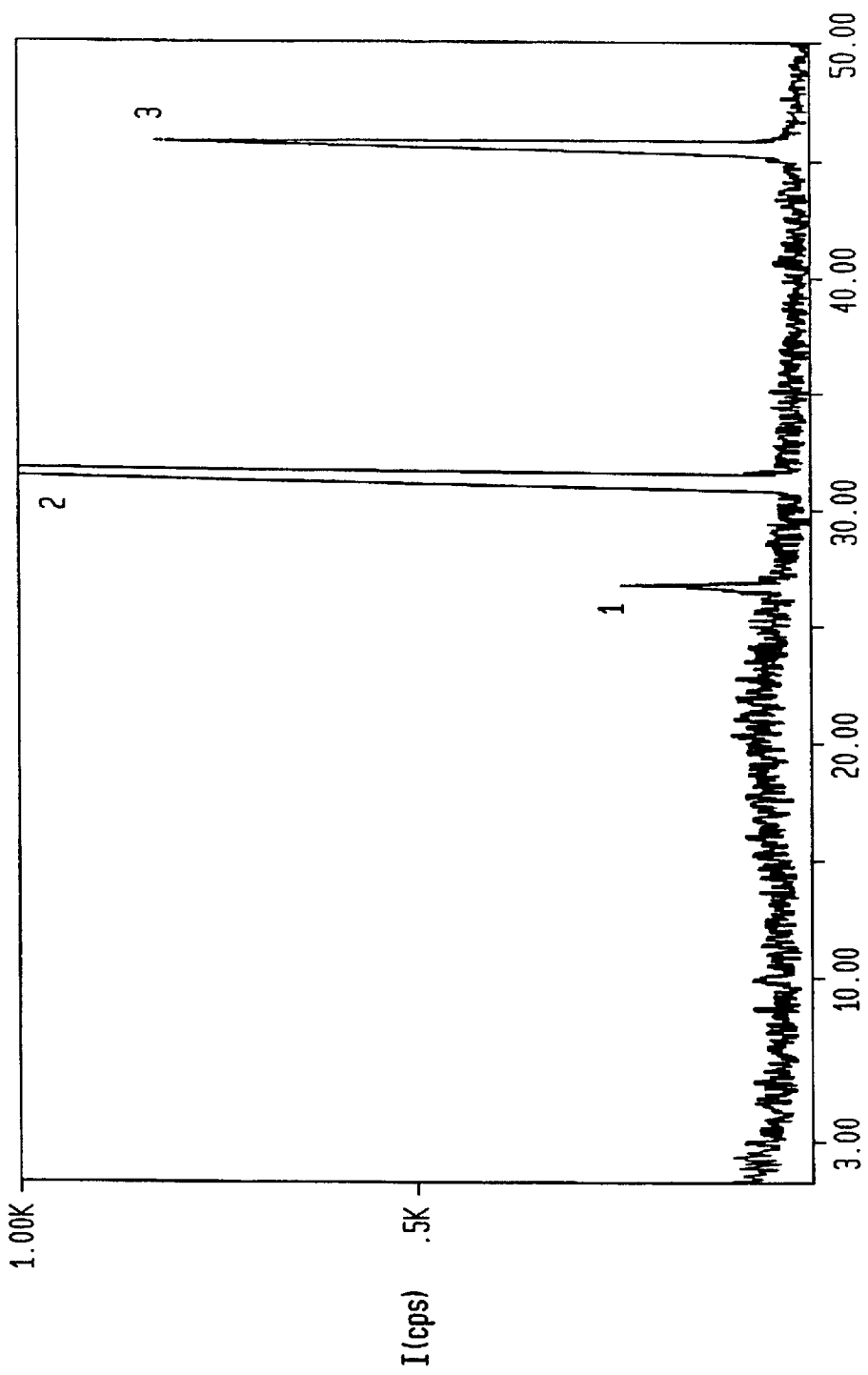
FIG. 5 is the XRD pattern of the amorphous cefuroxime axetil made in accordance with Example 1.

1.4 g of crystalline cefuroxime axetil S isomer and 0.6 g of sodium chloride were subjected to grinding using an agate pestle and mortar for a period of 10 hrs. X-ray diffraction (XRD) patterns of crystalline cefuroxime axetil S isomer, sodium chloride and the milled sample are shown in FIGS. 3, 4 and 5, respectively. The XRD pattern of FIG. 5 shows that the peaks characteristic of the crystalline form of cefuroxime axetil were either significantly decreased in intensity or entirely absent after milling. The XRD patterns thus demonstrate that cefuroxime axetil was converted to a predominantly amorphous form with crystallinity estimated to be less than 5%. The chromatographic purity of this sample was determined by HPLC and was found to be 99.31%.

EXAMPLE 2

Figure 6:
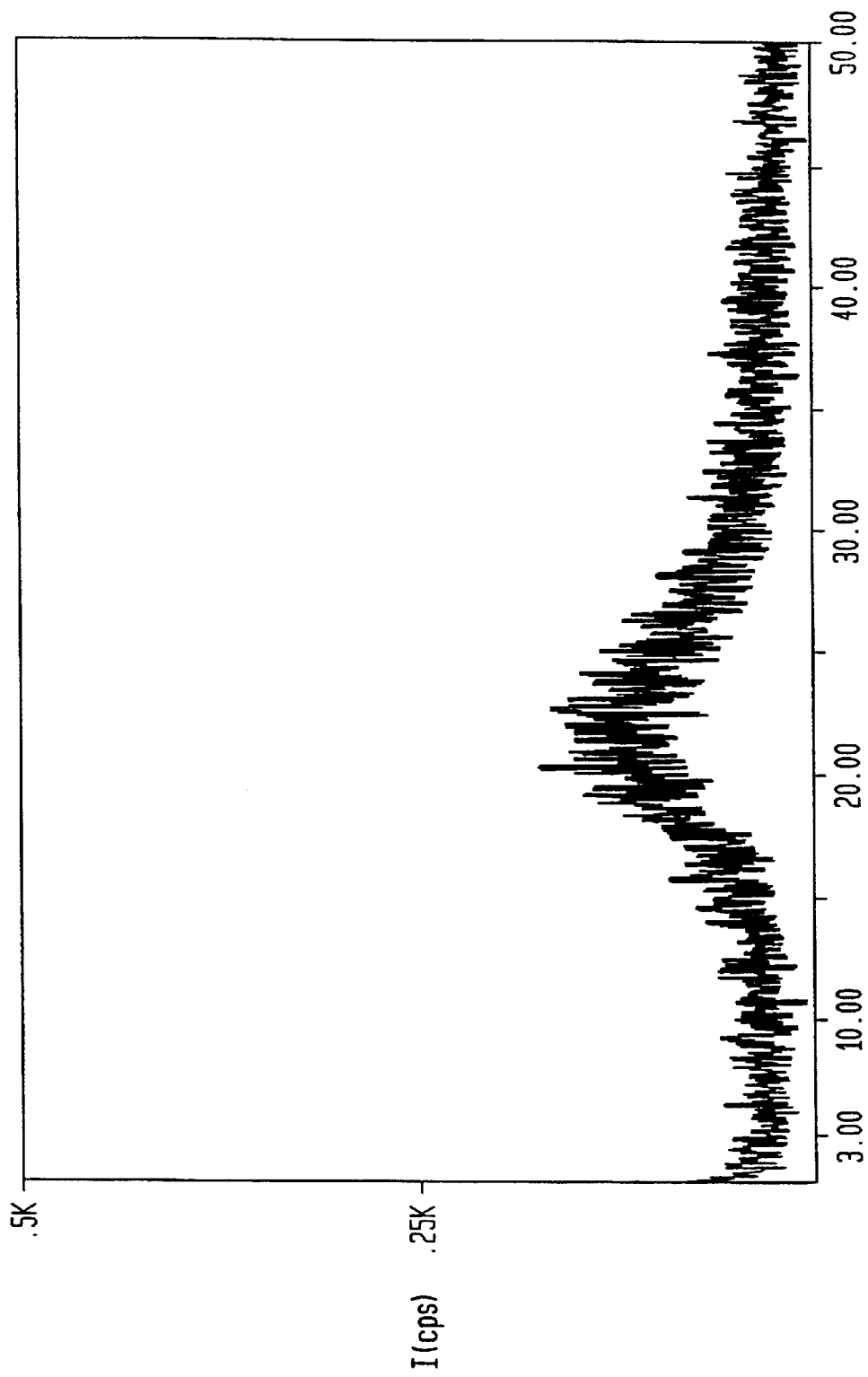
FIGS. 6–14 are XRD patterns of milled samples of cefuroxime axetil according to Examples 2–10.
Figure 7:
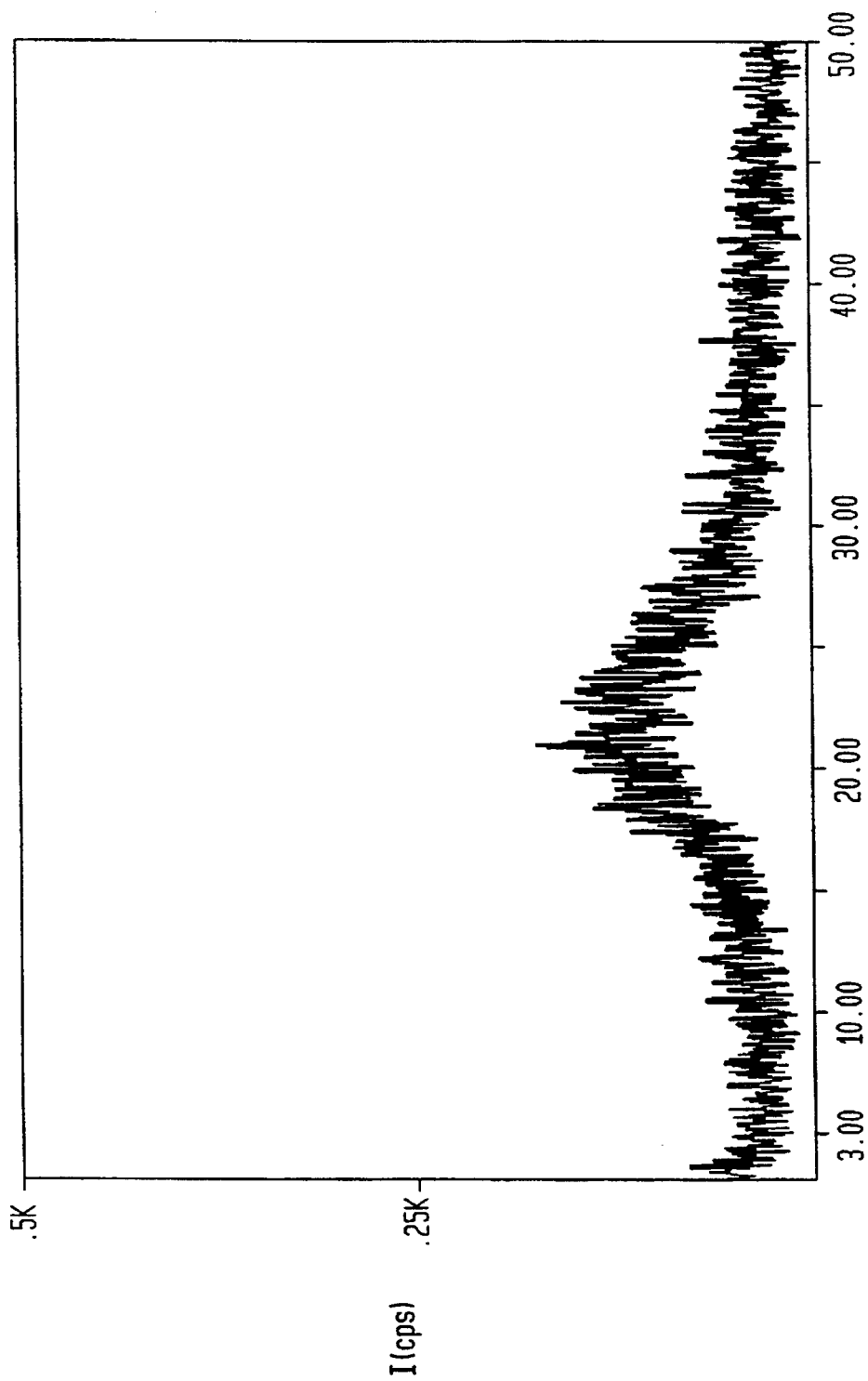
Figure 8:
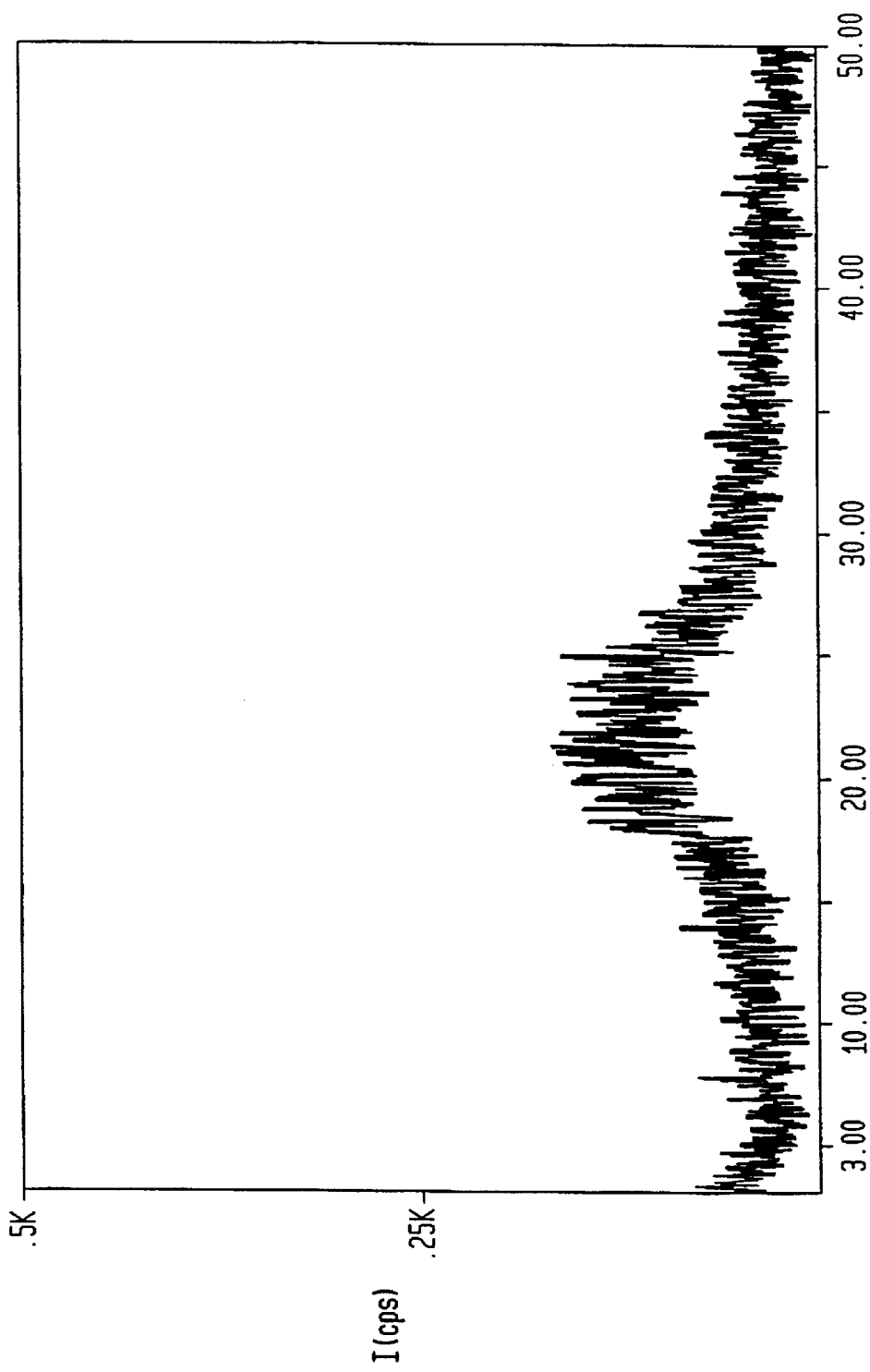
Figure 9:
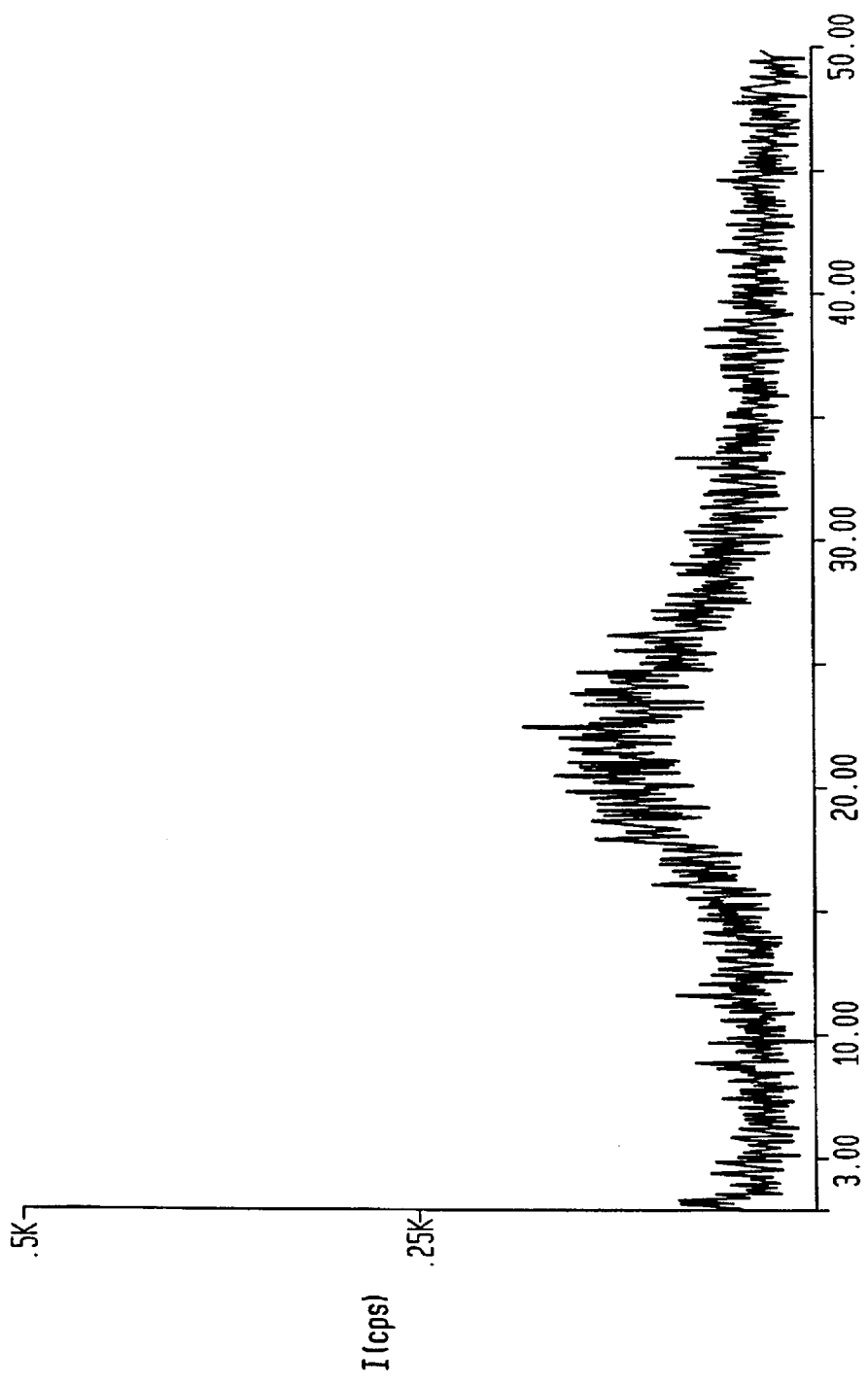
Figure 10:
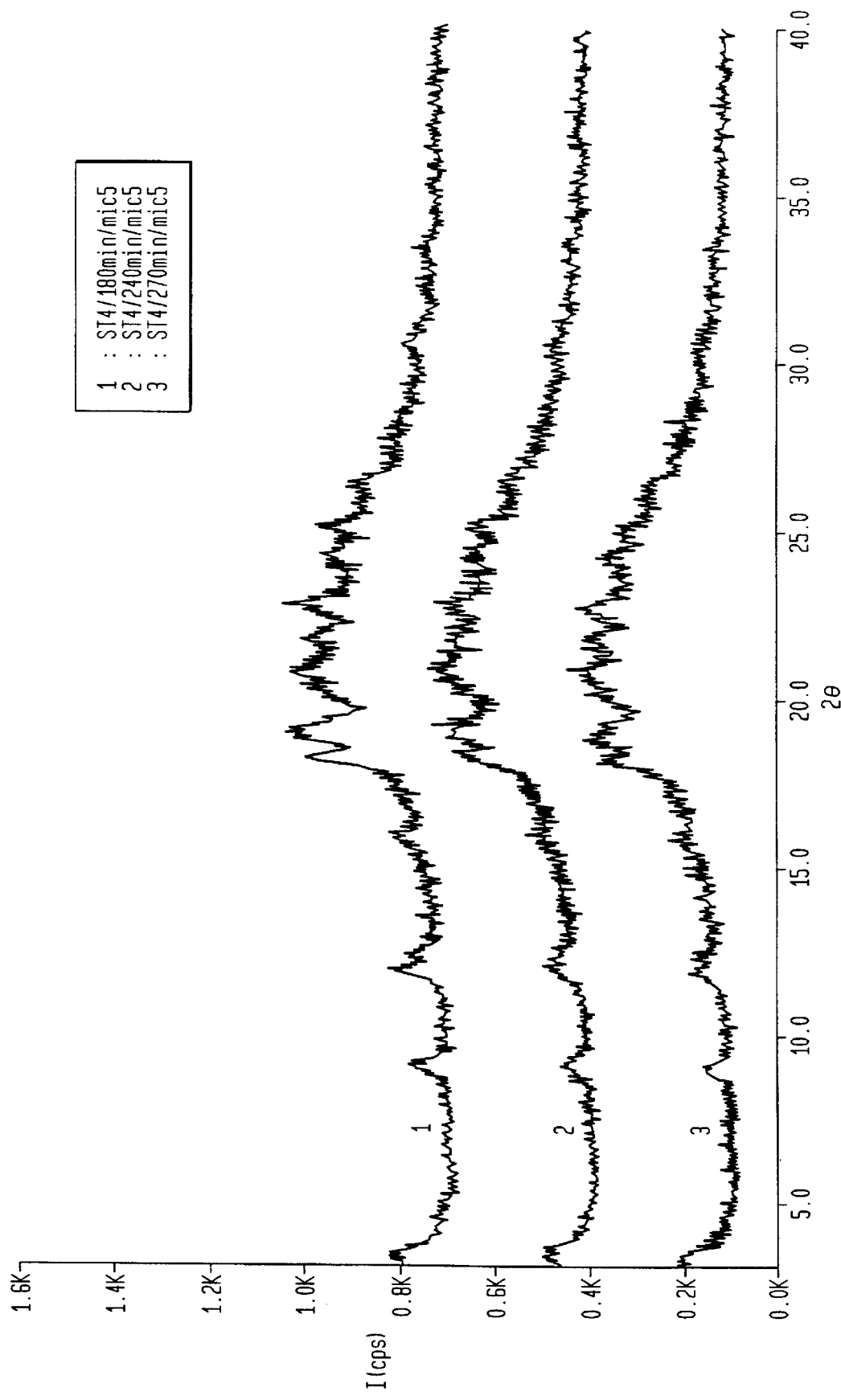
Figure 11:
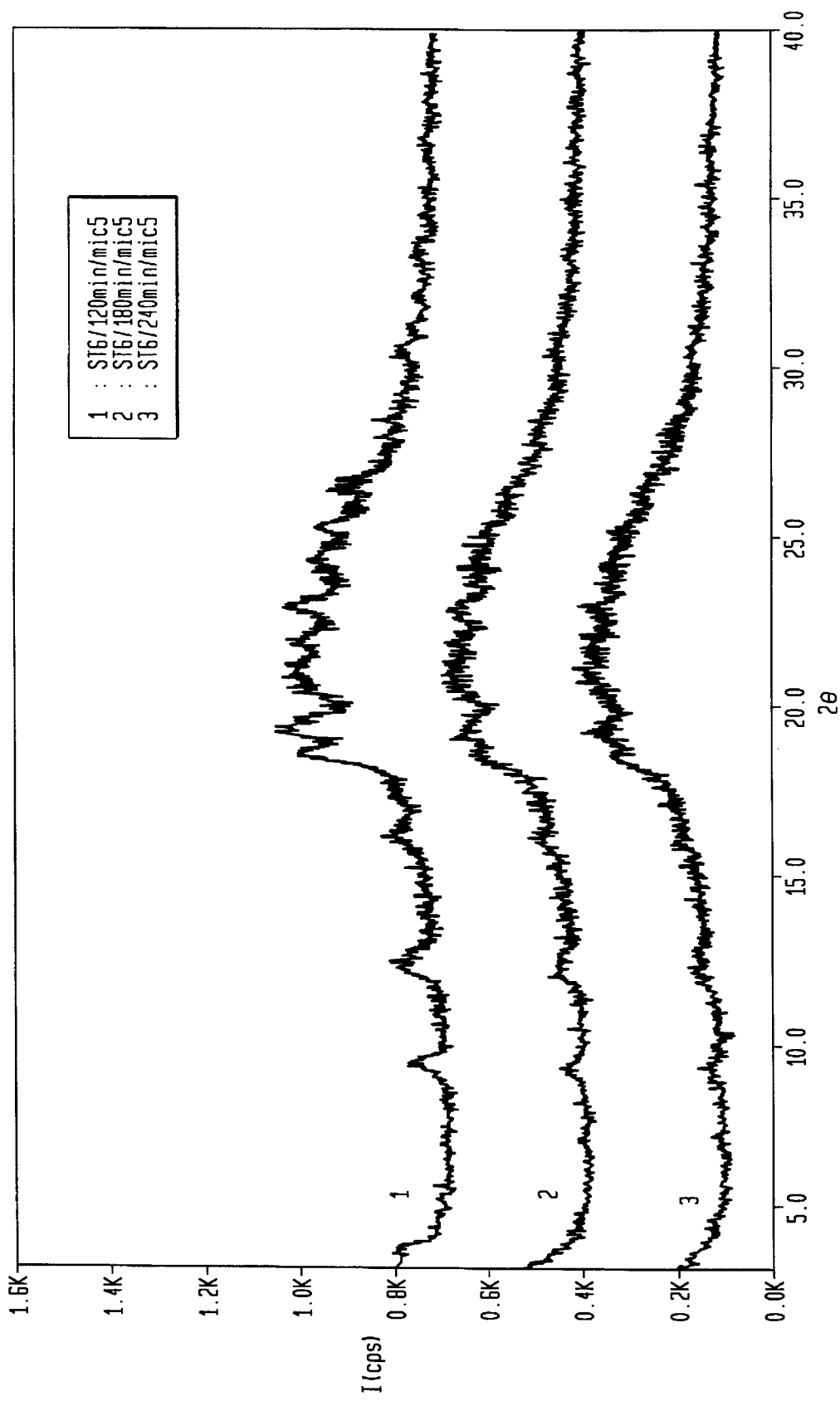
Figure 12:
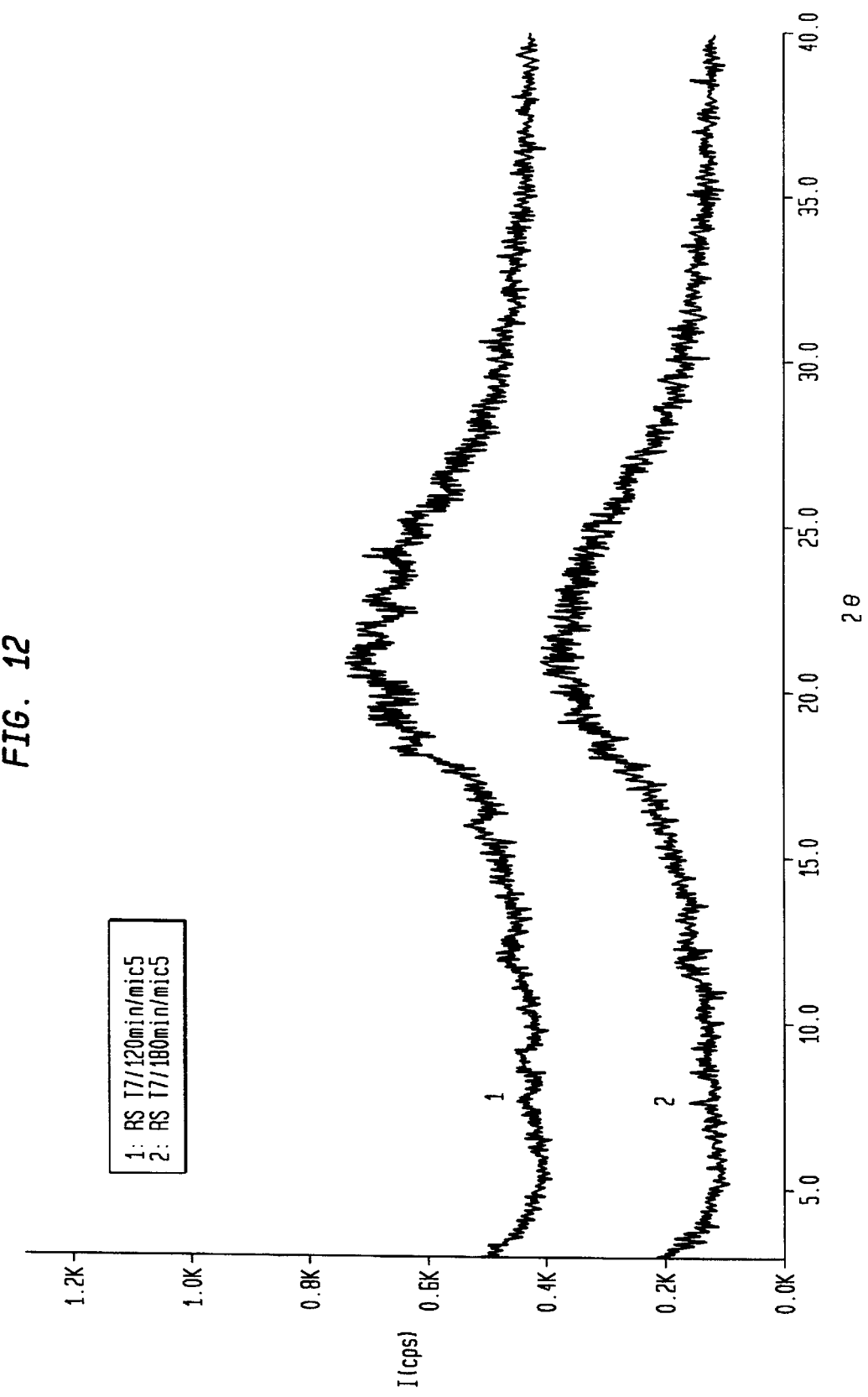
Figure 13:
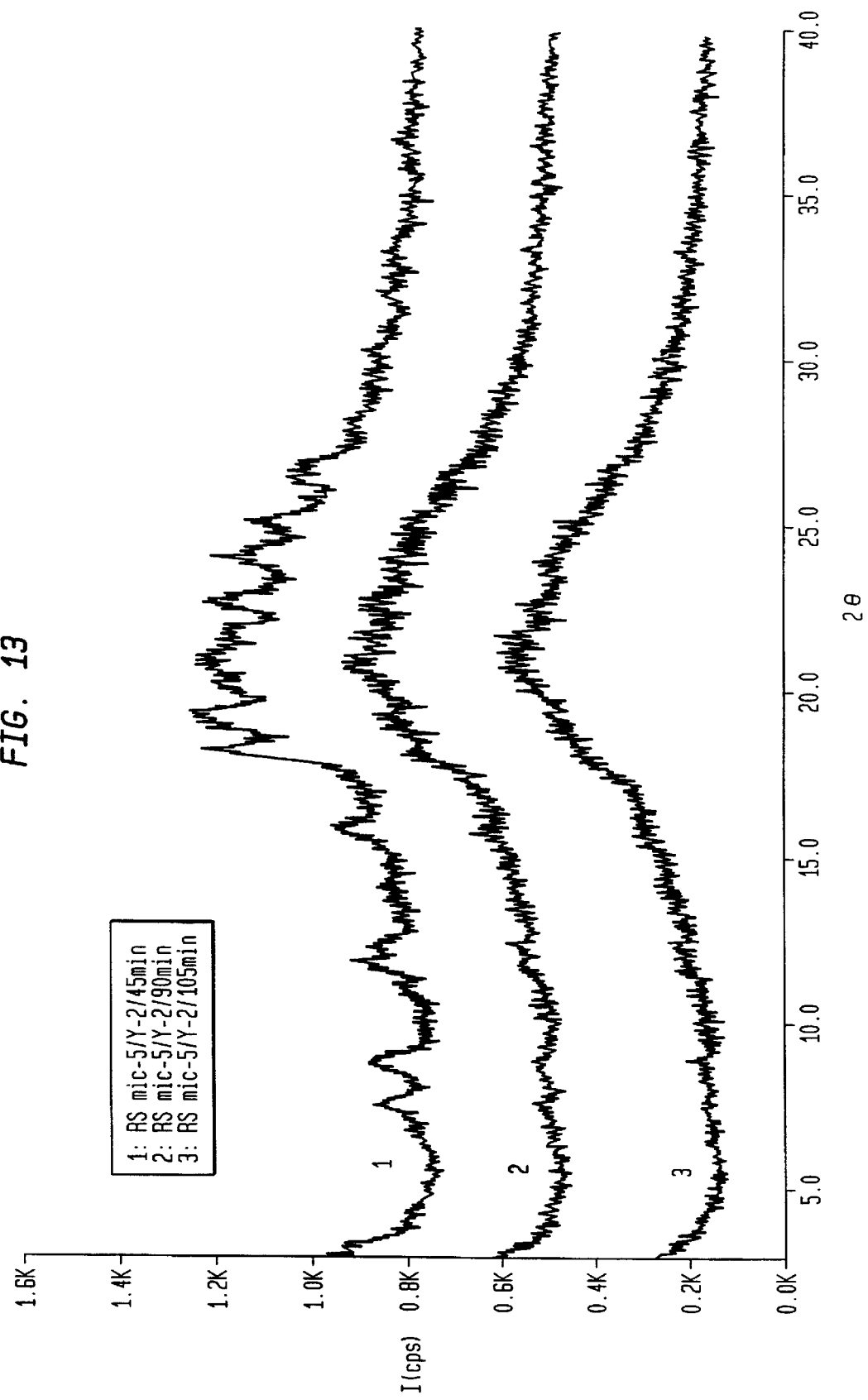

30 g of crystalline cefuroxime axetil S isomer with a particle size of 10–300 μm and having a bulk density of 0.391 g/cc, together with 3 g of sodium lauryl sulphate (SLS) were placed in the bowl of a Micros '0' Super Fine Mill. Cold water was circulated through the outer jacket. The mill was operated with main shaft rotation set at 1000 rpm for 120 mins. The inner temperature was maintained in the range from 19–24° C. The process details are given in Table 1 below. The milling proceeded smoothly during the run with the powder blend exhibiting good flow within the milling chamber. Samples of the material were examined by scanning electron microscopy and by X-ray diffraction crystallography. The particle size was found to be reduced to less than 2 μm. The X-ray diffraction pattern of the milled material is shown in FIG. 6. The XRD pattern shows that the peaks characteristic of the crystalline form of cefuroxime axetil were either significantly decreased in intensity or absent. The XRD pattern thus demonstrates that cefuroxime axetil was converted to a predominantly amorphous form with less than 5% estimated crystallinity. The total impurities (related substances) as determined by HPLC were found to be 1.129% m/m.

EXAMPLE 3–9

Crystalline cefuroxime axetil S isomer with a particle size of 10–300 μm and having a bulk density of 0.391 g/cc, a mixture of crystalline cefuroxime axetil S isomer with crystalline cefuroxime axetil R isomer with a particle size of 5–50 μm, and having a bulk density of 0.221 g/cc. and crystalline cefuroxime axetil R,S racemic mixture were tested for conversion from the crystalline form to an amorphous form in different trials. The process details are given in Table 1. The feed material consisted of cefuroxime axetil together with sodium lauryl sulphate or cefuroxime axetil together with sodium lauryl sulphate and colloidal silica (Aerosil 200). Samples of the material were withdrawn at various times for X-ray diffraction crystallography using a XRG 3000 diffractometer, and for scanning electron photomicrography. X-ray diffraction patterns of the samples are shown in FIGS. 7 to 13. Peaks characteristic of the crystalline form of the corresponding isomer(s) of cefuroxime axetil were either significantly decreased in intensity or absent. The XRD patterns thus demonstrate that as milling was continued, the degree of crystallinity progressively decreased until cefuroxime axetil was converted into a predominantly amorphous form. The percent crystallinity for the samples from Examples 6–9 was estimated to be less than 5% in all cases confirming the conversion of cefuroxime axetil to a predominantly (at least 95%) amorphous form. The total impurities (related substances) as determined by HPLC are given in Table 1.

The details for Examples 2–9 are summarized in the following Table.

| MACHINE TYPE | EXAMPLE NO. | GRINDING MEDIA VESSEL | TIME (min.) | REVOLUTIONS (RPM) | INNER TEMP. | FEED | OBSERVATIONS |
|---|---|---|---|---|---|---|---|
| MICROS '0' | 2 | ZrO$_2$ | 120 | 1,000 | 19–24° C. | Crystalline cefuroxime axetil S Isomer + SLS* (10:1) (33 g) | Good flow; Particle size of milled product < 2 μm. XRD (FIG. 6) confirms conversion. Total impurities (Related substances) by HPLC were 1.129% m/m. |
| | 3 | ZrO$_2$ | 120 | 1,000 | 22–23° C. | Crystalline cefuroxime axetil S Isomer + SLS + Aerosil 200** (100:10:1) (33.3 g) | Good flow; Particle size of milled product < 2 μm. XRD (FIG. 7) confirms conversion. Total impurities (Related substances) by HPLC were 1.113% m/m. |
| | 4 | ZrO$_2$ | 120 | 1,000 | 22–24° C. | Crystalline cefuroxime axetil S Isomer + Crystalline cefuroxime axetil R Isomer + SLS (5:5:1) (33 g) | Good flow; Particle size of milled product < 2 μm. XRD (FIG. 8) confirms conversion. Total impurities (Related substances) by HPLC were 1.07% m/m. |
| | 5 | ZrO$_2$ | 120 | 1,500 | 26° C. | Crystalline cefuroxime axetil S Isomer + SLS (10:1) (33 g) | Good flow; Particle size of milled product < 2 μm. XRD (FIG. 9) confirms conversion. Total impurities (Related substances) by HPLC were 1.295% m/m |
| MICROS '5' | 6 | ZrO$_2$ | 240 | 500 | 22–25° C. | Crystalline cefuroxime axetil S Isomer + SLS (10:1) + Aerosil 200 (2%) (280 g) | Premix in Nara Mixer Granulator for 2 min. XRD (FIG. 10) confirms conversion. Particle size of milled product < 2 μm. Total impurities (Related substances) by HPLC were 1.897% m/m. |
| | 7 | ZrO$_2$ | 240 | 500 | 22–23° C. | Crystalline cefuroxime axetil S Isomer + SLS (10%) + Aerosil 200 (2%) (270 g) | Premix in Nara Mixer Granulator for 2 min Good flow observed. Particle size of milled product < 2 μm. XRD (FIG. 11) confirms conversion. Total impurities (Related substances) |

-continued

PROCESS PARAMETERS

| MACHINE TYPE | EXAMPLE NO. | GRINDING MEDIA VESSEL | TIME (min.) | REVOLUTIONS (RPM) | INNER TEMP. | FEED | OBSERVATIONS |
|---|---|---|---|---|---|---|---|
| | 8 | ZrO$_2$ | 180 | 500 | 22–25° C. | Crystalline cefuroxime axetil S Isomer + SLS (10%) + Aerosil 200 (2%) (280 g) | by HPLC were 1.235% m/m. Premix in Nara Mixer Granulator for 2 min Good flow observed. Particle size of milled product < 2 μm. XRD (FIG. 12) confirms conversion. Total impurities (Related substances) by HPLC were 2.492% m/m |
| | 9 | ZrO$_2$ | 105 | 600 | 21–24° C. | Crystalline cefuroxime axetil S Isomer + SLS (10%) + Aerosil 200 (2%) (280 g) | Premix in Nara Mixer Granulator for 2 min. Good flow observed XRD (FIG. 13) confirms conversion. Total impurities (Related substances) by HPLC were 1.777% m/m. |

*SLS = sodium lauryl sulphate.
**Aerosil 200 is a commercial grade of colloidal silica.

EXAMPLE 10

Figure 14:
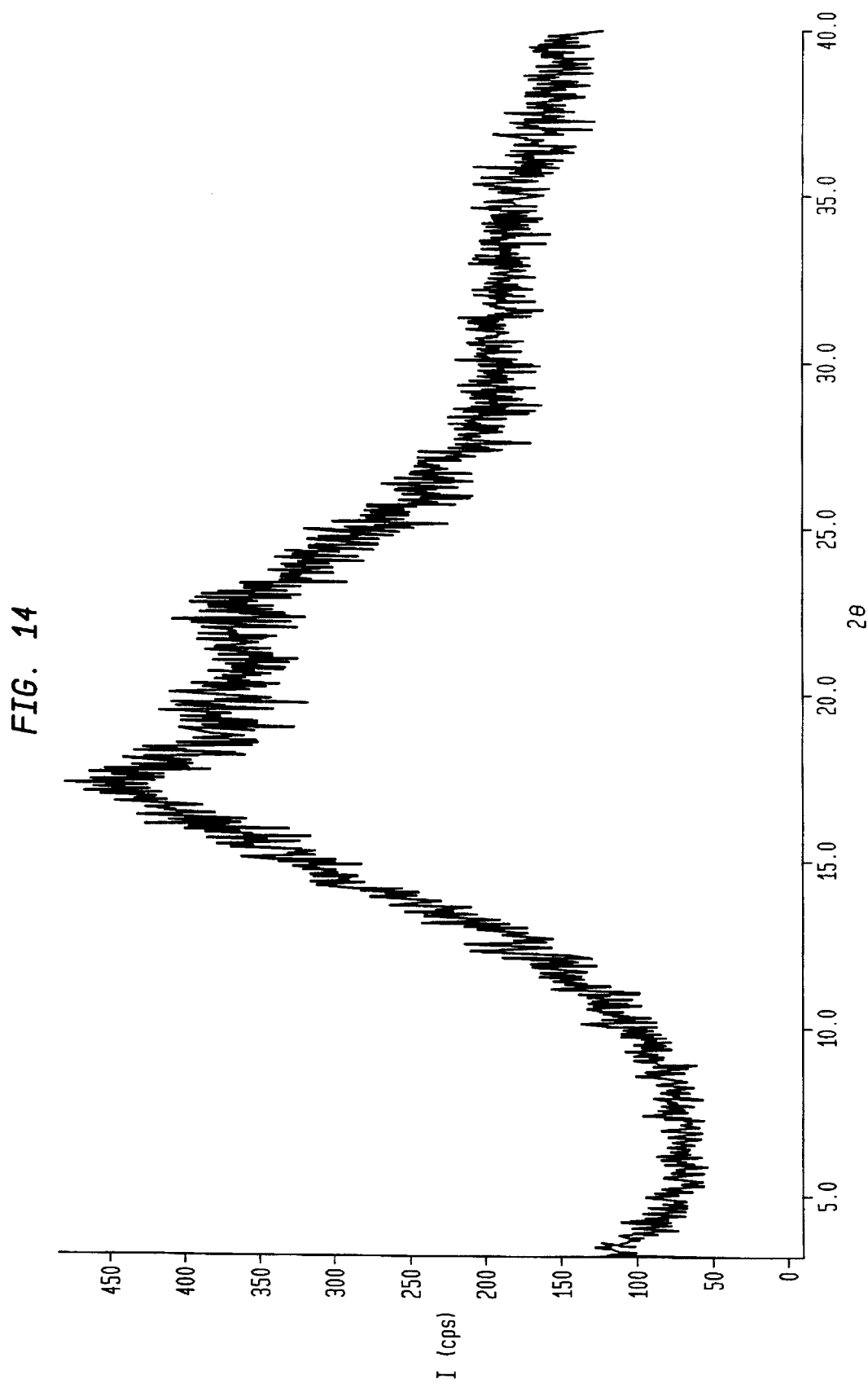

30 g of crystalline cefuroxime axetil R,S racemic mixture and 70 g of potato starch were processed in a Nara Hybridization System, Model NHS-1 (Nara Machinery Co., Ltd., Japan), for 1 hr. with the outer edges of the blades rotating at 80 ms$^{-1}$. The inner surface of the hybridization chamber was cooled by water circulation through the outer jacket. The XRD pattern of the sample collected after 30 min. of milling is shown in FIG. 14. The XRD pattern confirms the conversion of cefuroxime axetil into a substantially amorphous form. The total impurities (related substances) as determined by HPLC were found to be 2.803% m/m.

While the invention has been described by reference to specific embodiments, this was for purposes of illustration only. Numerous alternative embodiments will be apparent to those skilled in the art and are considered to be within the scope of the invention.

What is claimed is:

1. A pharmaceutical composition comprising cefuroxime axetil and calcium carbonate, wherein the ratio of cefuroxime axetil to calcium carbonate is in the range of about 1:7 to about 3:2.

2. The composition of claim 1 wherein the ratio of cefuroxime axetil to calcium carbonate is in the range of about 1:4 to about 1:1.

3. The composition of claim 1, the cefuroxime axetil comprises milled particles of particle size less than about 2 μm.

4. The composition of claim 1, further comprising a pharmaceutical excipient selected from the group consisting of sodium lauryl sulphate, colloidal silica, talc, sodium chloride, starch, and mixtures thereof.

5. The composition of claim 1, wherein the cefuroxime axetil substantially comprises one of the individual R or S diastereomers of cefuroxime axetil.

6. The composition of claim 1, wherein the cefuroxime axetil comprises a mixture of the R and S diastereomers of cefuroxime axetil.

* * * * *